United States Patent
Sankai (10) Patent No.: US 12,251,230 B2
(45) Date of Patent: Mar. 18, 2025

(54) DIAGNOSIS SUPPORT SYSTEM AND DIAGNOSIS SUPPORT METHOD

(71) Applicant: CYBERDYNE Inc., Ibaraki (JP)

(72) Inventor: Yoshiyuki Sankai, Ibaraki (JP)

(73) Assignee: CYBERDYNE Inc., Ibaraki (JP)

( * ) Notice: Subject to any disclaimer, the term of this patent is extended or adjusted under 35 U.S.C. 154(b) by 392 days.

(21) Appl. No.: 17/764,103

(22) PCT Filed: Sep. 29, 2020

(86) PCT No.: PCT/JP2020/036893
§ 371 (c)(1),
(2) Date: Mar. 25, 2022

(87) PCT Pub. No.: WO2021/070678
PCT Pub. Date: Apr. 15, 2021

(65) Prior Publication Data
US 2022/0378355 A1 Dec. 1, 2022

(30) Foreign Application Priority Data
Oct. 7, 2019 (JP) .................................. 2019-184841

(51) Int. Cl.
| | |
|---|---|
| A61B 5/36 | (2021.01) |
| A61B 5/00 | (2006.01) |
| A61B 5/28 | (2021.01) |
| A61B 5/339 | (2021.01) |
| A61B 5/352 | (2021.01) |
| A61B 5/361 | (2021.01) |

(52) U.S. Cl.
CPC .............. *A61B 5/361* (2021.01); *A61B 5/28* (2021.01); *A61B 5/339* (2021.01); *A61B 5/352* (2021.01); *A61B 5/4842* (2013.01)

(58) Field of Classification Search
CPC ........ G16H 40/63; G16H 50/20; G16H 50/30; G16H 50/70; A61B 5/28; A61B 5/339; A61B 5/352; A61B 5/361; A61B 5/4842; A61B 5/7267
See application file for complete search history.

(56) References Cited

U.S. PATENT DOCUMENTS

9,456,759 B2 * 10/2016 Lian ....................... A61B 5/316
2017/0156614 A1 * 6/2017 Ibáñez Català .... A61B 5/02405

FOREIGN PATENT DOCUMENTS

| JP | 2018-153487 A | 10/2018 |
|---|---|---|
| JP | 2019-502437 A | 1/2019 |
| JP | 2019-129954 A | 8/2019 |

OTHER PUBLICATIONS

Patent Cooperation Treaty, International Search Report, Application No. PCT/JP2020/036893, dated Oct. 27, 2020, in 5 pages.

* cited by examiner

*Primary Examiner* — Amanda K Hulbert
(74) *Attorney, Agent, or Firm* — Procopio, Cory, Hargreaves & Savitch LLP (57) ABSTRACT

The degree of progress of an atrial fibrillation which a subject suffers from is assessed and learned on the basis of a frequency histogram according to an occurrence frequency based on judgment results of a complex fractionated atrial electrogram for a specified period of time, which are obtained from the subject's electrocardiogram data.

10 Claims, 7 Drawing Sheets

DIAGNOSIS SUPPORT SYSTEM AND DIAGNOSIS SUPPORT METHOD

CROSS-REFERENCE TO RELATED APPLICATIONS

This application is US National Stage of International Patent Application PCT/JP2020/036893, filed Sep. 29, 2020, which claims benefit of priority from Japanese Patent Application JP2019-184841, filed Oct. 7, 2019, the contents of both of which are incorporated herein by reference.

TECHNICAL FIELD

The present invention relates to a diagnosis support system and a diagnosis support method and is particularly suited for application to a diagnosis support system and diagnosis support method for judging a continuous atrial fibrillation while monitoring an arrhythmia of a heart.

BACKGROUND ART

The atrial fibrillation is a severe disease which causes cardiac insufficiency and a cerebral infarction that rank high in causes of death in our country. An example of an effective treatment for the atrial fibrillation is a percutaneous catheter myocardial ablation. This percutaneous catheter myocardial ablation is a surgical operation conducted by a doctor to judge an ablation site on the basis of an electrocardiogram measured inside a heart and to treat the atrial fibrillation by electrically causing necrosis of cells by using high-frequency electric conduction.

It has been conventionally known that a measured site of complex fractionated atrial electrograms (CFAEs: Complex Fractionated Atrial Electrograms) as the ablation site of the percutaneous catheter myocardial ablation is an important target.

The complex fractionated atrial electrograms: are an electrocardiogram signal regarding which one or more characteristics of two characteristics exist, that is, atrial waves which occur with short intervals of less than 120 [ms], and a continuous electric potential that is an atrial electric potential regarding which the electric potential occurs continuously; and contribute to continuance of the atrial fibrillation.

There have conventionally been proposed automatic judgments of the complex fractionated atrial electrograms for the percutaneous catheter myocardial ablation by means of a frequency analysis and a threshold value judgment other than a method of checking with a visual sense. These methods using the frequency analysis and the threshold value judgment make it possible to judge the atrial waves with short intervals, which is one of characteristics of the complex fractionated atrial electrogram.

However, the ablation to the site where the electric potential occurs continuously and the continuous electric potential which is the atrial electric potential is measured is effective as an ablation target of the percutaneous catheter myocardial ablation, but the current situation is that a means of performing the automatic judgment has not been established yet.

As a conventional atrial fibrillation detection method, there has been proposed an atrial fibrillation judgment apparatus designed to: extract irregular pulse waves having occurrence intervals not within a preset occurrence interval judgment range centered on an average occurrence interval, which is an average of all occurrence intervals, among a plurality of pulse waves; and determine that the atrial fibrillation of a living body has occurred if a ratio of the number of irregular pulse waves to the number of all the occurrence intervals of the plurality of pulse waves is larger than a preset anomaly occurrence interval occurrence ratio judgment value (see PTL 1).

Furthermore, a heartbeat interval between each heartbeat, which is a biological signal related to a user's heart activities, and its immediately preceding heartbeat is created as a continuous heartbeat interval sequence; the heartbeat interval sequence is divided into a plurality of limited sequence segments, each of which has a given temporal length composed of a continuous heartbeat interval; and a scatter diagram indicating distribution of data related to the heartbeat interval sequence is created for each sequence segment and the sequence segment is encrypted.

Then, the scatter diagram is encrypted by creating a histogram indicating the quantity of plot points which are plotted in each specific area of the scatter diagram, and the histogram is normalized by dividing a pin count of each pin (pins with a default width and a default quantity included in the histogram) by a total number of plot points of the scatter diagram, thereby proposing a method for analyzing and identifying signs of the user's atrial fibrillation, which is designed to decide a probability of the sequence segment being a rhythm of the atrial fibrillation or a rhythm of a non-atrial fibrillation (see PTL 2).

Furthermore, there is proposed an atrial fibrillation detection system for detecting whether a subject has the atrial fibrillation or not by removing improper heartbeat intervals, which are not derived from the heartbeats of the subject's heart, from heartbeat interval data obtained by measuring the heartbeat intervals of the subject's heart, judging whether the atrial fibrillation has occurred or not by using the data after the removal, and displaying the judgment result on a display means (see PTL 3).

CITATION LIST

Patent Literature

PTL 1: Japanese Patent Application Laid-Open (Kokai) Publication No. 2018-153487
PTL 2: Japanese Unexamined Patent Application Publication (Translation of PCT Application) No. 2019-502437
PTL 3: Japanese Patent Application Laid-Open (Kokai) Publication No. 2019-129954

SUMMARY OF THE INVENTION

Problems to be Solved by the Invention

Meanwhile, PTL 1 is the means for judging whether the atrial fibrillation has occurred or not according to the ratio of the number of anomaly occurrence interval heartbeat synchronous waves to the number of a plurality of heart beat synchronous waves; and since the preset reference range is set as a threshold value, there is a limit to enhancement of judgment accuracy.

Moreover, PTL 2 decides the probability of the sequence segment based on the continuous heartbeat interval being the rhythm of the atrial fibrillation or the rhythm of the non-atrial fibrillation by using an artificial neural network; however, it does not include an actual judgment result by a doctor(s) and just attempts to enhance the accuracy of an algorithm for detecting the rhythm of the atrial fibrillation.

Furthermore, PTL 3 just detects whether a signal fibrillation exists or not by removing the improper heartbeat intervals from the heartbeat intervals or the heart and has nothing to do with the actual judgment result by the doctor(s).

Practically, there are few cases where patients themselves recognize symptoms of the atrial fibrillation, and it is necessary for the doctor to measure the heartbeat intervals for a period of time such as one month in order to assess the symptoms, so that there are many cases where the patients' assessment and the doctor's assessment become ambiguous.

The present invention was devised in consideration of the above-described circumstances and proposes a diagnosis support system and diagnosis support method for supporting a doctor(s) so that they can accurately diagnose the continuous atrial fibrillation.

Means to Solve the Problems

In order to solve the above-described problems, there is provided according to the present invention a diagnosis support system including: an electrocardiogram measurement unit that measures an electrocardiogram of a subject; a complex fractionated atrial electrogram judgment unit that judges a complex fractionated atrial electrogram indicating characteristics of an atrial fibrillation at a heartbeat interval that is a peak interval of R waves which are chronologically adjacent to each other, on the basis of electrocardiogram data measured by the electrocardiogram measurement unit; a data storage unit that stores judgment results by the complex fractionated atrial electrogram judgment unit in chronological order as judgment data which is specific to the subject; a frequency histogram generation unit that generates a frequency histogram according to an occurrence frequency within a specified period of time on the basis of the judgment data which is collected over the specific period of time with respect to the subject and read from the data storage unit; and an assessment learning unit that performs assessment learning to assess a degree of progress of an atrial fibrillation, which the subject suffers from, on the basis of the frequency histogram with respect to the subject by the frequency histogram generation unit.

This diagnosis support system is designed to assess and learn the degree of progress of the atrial fibrillation, which the subject suffers from, on the basis of the frequency histogram according to the occurrence frequency based on the judgment result of the complex fractionated atrial electrograms for the specified period of time, which is obtained from the electrocardiogram data of the subject. Therefore, it becomes possible to support the doctor(s) so that they can accurately diagnose the atrial fibrillation even under the condition where the subject themselves cannot recognize the continuous atrial fibrillation.

Moreover, according to the present invention, the complex fractionated atrial electrogram judged by the complex fractionated atrial electrogram judgment unit is a combination of an occurrence frequency of atrial waves and an atrial electric potential which occurs continuously. As a result, the diagnosis support system can automatically judge the complex fractionated atrial electrograms (CFAEs), which are a measurement index for finding an ablation site of the percutaneous catheter myocardial ablation.

Furthermore, the present invention is designed to include: a display unit that displays the frequency histogram with respect to the subject by the frequency histogram generation unit; an input unit for a doctor to input the degree of progress of the atrial fibrillation, which the subject concerned suffers from, as a diagnosis result with respect to the frequency histogram displayed on the display unit; and a criterion function generation unit that generates a criterion function indicating a criterion for assessing the degree of progress of the atrial fibrillation by referring to a result of the assessment learning by the assessment learning unit and the diagnosis result of the doctor by the input unit with respect to the subject.

As a result, with the diagnosis support system, the doctor inputs the degree of progress of the subject's atrial fibrillation over a specified period of time via the input unit while visually checking the subject's frequency histogram displayed on the display unit, thereby making it possible to significantly enhance the accuracy of the assessment learning for assessing the degree of progress of the atrial fibrillation which the subject suffers from.

Furthermore, there is provided according to the present invention a diagnosis support method including: a first step of judging a complex fractionated atrial electrogram indicating characteristics of an atrial fibrillation at a heartbeat interval that is a peak interval of R waves which are chronologically adjacent to each other, on the basis of electrocardiogram data obtained by measuring an electrocardiogram of a subject; a second step of storing judgment results by the first step as judgment data, which is specific to the subject, in chronological order in a data storage unit; a third step of generating a frequency histogram according to an occurrence frequency within a specified period of time on the basis of the judgment data which is collected over the specific period of time with respect to the subject and read from the data storage unit; and a fourth step of performing assessment learning to assess a degree of progress of an atrial fibrillation, which the subject suffers from, on the basis of the frequency histogram with respect to the subject by the third step.

As a result, this diagnosis support method is designed to assess and learn the degree of progress of the atrial fibrillation, which the subject suffers from, on the basis of the frequency histogram according to the occurrence frequency based on the judgment result of the complex fractionated atrial electrograms for the specified period of time, which is obtained from the electrocardiogram data of the subject. Therefore, it becomes possible to support the doctor(s) so that they can accurately diagnose the atrial fibrillation even under the condition where the subject themselves cannot recognize the continuous atrial fibrillation.

Advantageous Effects of the Invention

According to the present invention as described above, it is possible to implement the diagnosis support system and the diagnosis support method which are capable of supporting a doctor(s) so that they can accurately diagnose the degree of progress of the atrial fibrillation without giving physical load to the subject.

DESCRIPTION OF EMBODIMENTS

An embodiment of the present invention will be described below in detail with reference to the drawings.

Figure 1:
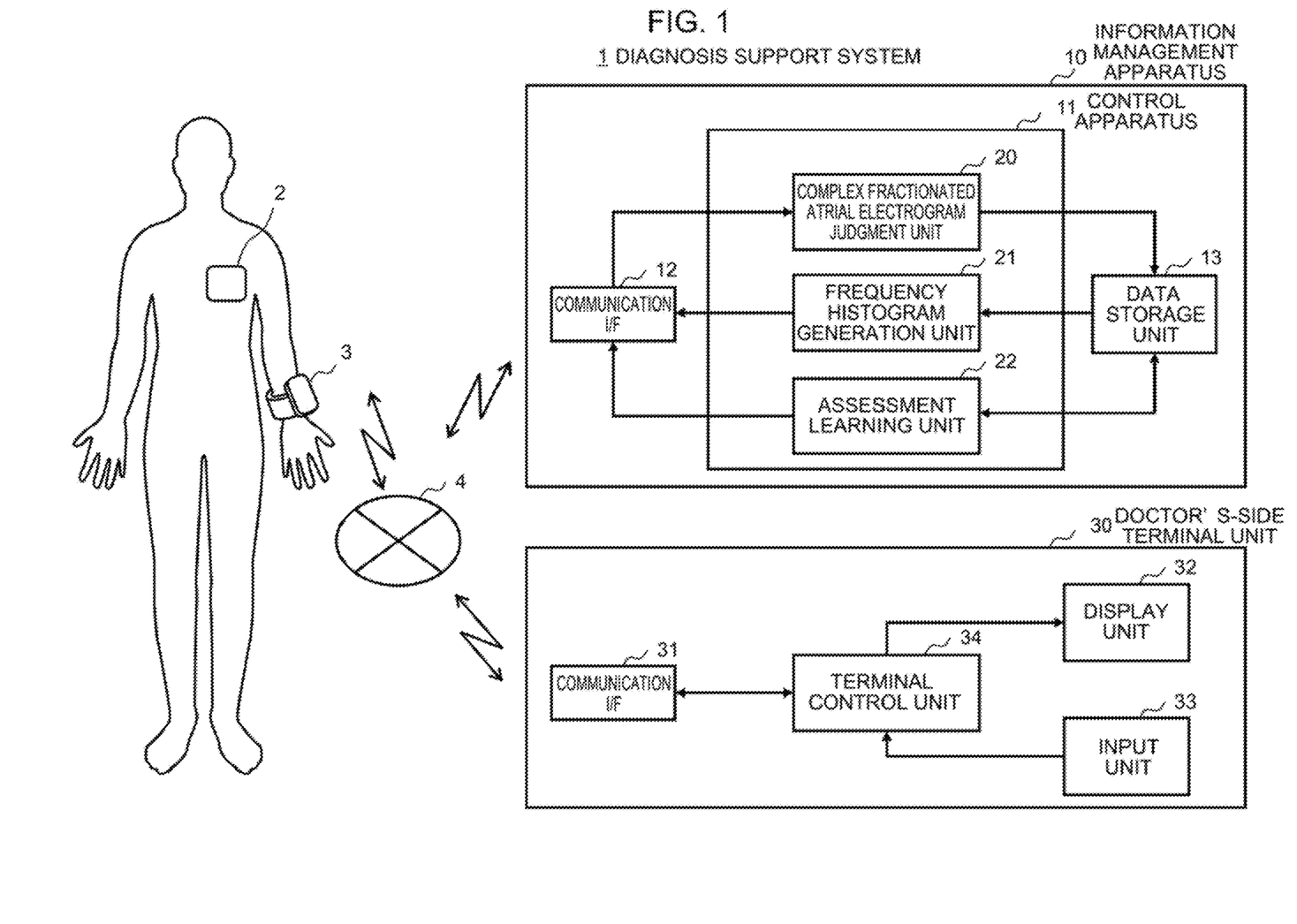
FIG. 1 is a block diagram illustrating an overall configuration of a diagnosis support system according to an embodiment of the present invention.

(1) Configuration of Diagnosis Support System According to the Present Invention Referring to FIG. 1, a diagnosis support system 1 according to this embodiment includes an electrocardiogram sensor (electrocardiogram measurement unit) 2 composed of a plurality of electrodes mounted noninvasively on a subject's left chest, and a communication terminal unit 3 mounted on the subject's wrist.

The electrocardiogram sensor 2 continuously measures an electrocardiogram indicating an activity electric potential which occurs due to excitation of the subject's cardiac muscles and transmits electrocardiogram data which is the measurement result to the communication terminal unit 3 of a watch type wirelessly or in a wired manner. The communication terminal unit 3 stores the electrocardiogram data in an internal memory (which is not illustrated in the drawing) and transmits it to an information management apparatus 10 with which communications can be performed via a communication network 4 such as the Internet.

The information management apparatus 10 includes: a control apparatus 11 which is composed of a CPU (Central Processing Unit) for controlling the entire apparatus; and a data storage unit 13 which stores the electrocardiogram data received by a communication interface 12 from the communication unit 3 via the communication network 4.

Figure 2:
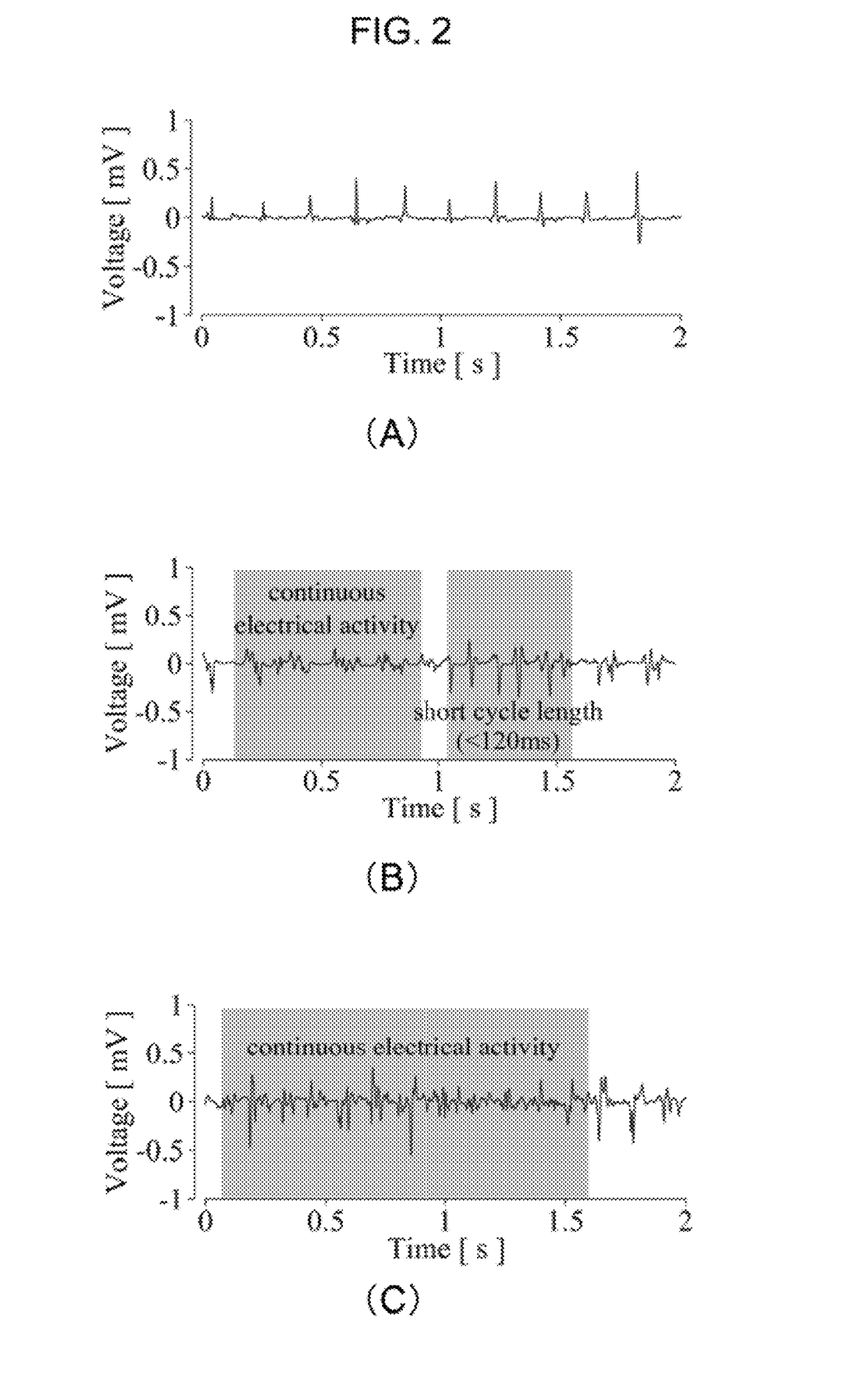
FIG. 2 is a block diagram illustrating the configuration of a control apparatus for an information management apparatus illustrated in FIG. 1.

The control apparatus 11 includes a complex fractionated atrial electrogram judgment unit 20, a frequency histogram generation unit 21, and an assessment learning unit 22. The complex fractionated atrial electrogram judgment unit 20 judges a complex fractionated atrial electrogram indicating characteristics of the atrial fibrillation at a heartbeat interval that is a peak interval of R waves which are chronologically adjacent to each other, on the basis of the electrocardiogram data received via the communication interface 12 and stores the judgment result, as judgment data which is specific to the subject, in the data storage unit 13.

The frequency histogram generation unit 21 generates a frequency histogram according to an occurrence frequency during a specified period of time on the basis of the judgment data which was collected over the specified period of time with respect to the subject and is read from the data storage unit 13.

The assessment learning unit 22 performs assessment learning to assess the degree of progress of the atrial fibrillation, which the subject suffers from, on the basis of the frequency histogram with respect to the subject by the frequency histogram generation unit 21.

Furthermore, with the diagnosis support system 1, a doctor's-side terminal unit 30 for the doctor to diagnose the degree of progress of the atrial fibrillation of the subject, in addition to the information management apparatus 10, is wirelessly connected to the communication network 4. This doctor's-side terminal unit 30 is a touch-panel-type wireless communication terminal and includes a display unit 32 which displays videos or the like based on various kinds of information received via a communication interface 31, a touch-panel-type input unit 33 capable of input operations by touching it with a fingertip, and a terminal control unit 34 which integrally controls this entire terminal.

(2) Diagnosis Support Processing at Control Apparatus

Now, FIG. 2(A) to FIG. 2(C) illustrate electrocardiograms measured by the electrocardiogram sensor 2. The electrocardiogram of the complex fractionated atrial electrogram which is characterized in that atrial waves are measured at intervals of 120 [ms] or more and regarding which the atrial fibrillation has not occurred is indicated in FIG. 2(A); and the electrocardiograms of the complex fractionated atrial electrograms regarding which two characteristics, that is, the atrial waves with short intervals and the continuous electric potential can be confirmed are indicated respectively in FIG. 2(B) and FIG. 2(C).

Regarding the percutaneous catheter myocardial ablation, ventricle waves are sometimes measured at the same time as the atrial electric potential in the electrocardiogram measured from the atrium on which the judgment of the complex fractionated atrial electrogram is performed. Since the ventricle waves do not contribute to the continuous atrial fibrillation, the ventricle waves are removed from the electrocardiogram signal measured at the atrium by using the ventricle waves measured at a body surface.

An atrial wave interval judgment algorithm described later is used for the judgment of the ventricle waves measured at the body surface. Excitation time of the ventricle waves to be removed is from 60 [ms] to 100 [ms]. The complex fractionated atrial electrogram judgment unit 20 for the control apparatus 11 finds a maximum value of each ventricle wave at the body surface, which is judged by the atrial wave interval judgment algorithm, and sets the electric potential measured 30 [ms] before and after the time when the maximum value of each ventricle wave was judged, to 0 [mV] with respect to the electric potential measured at the atrium.

Figure 3:
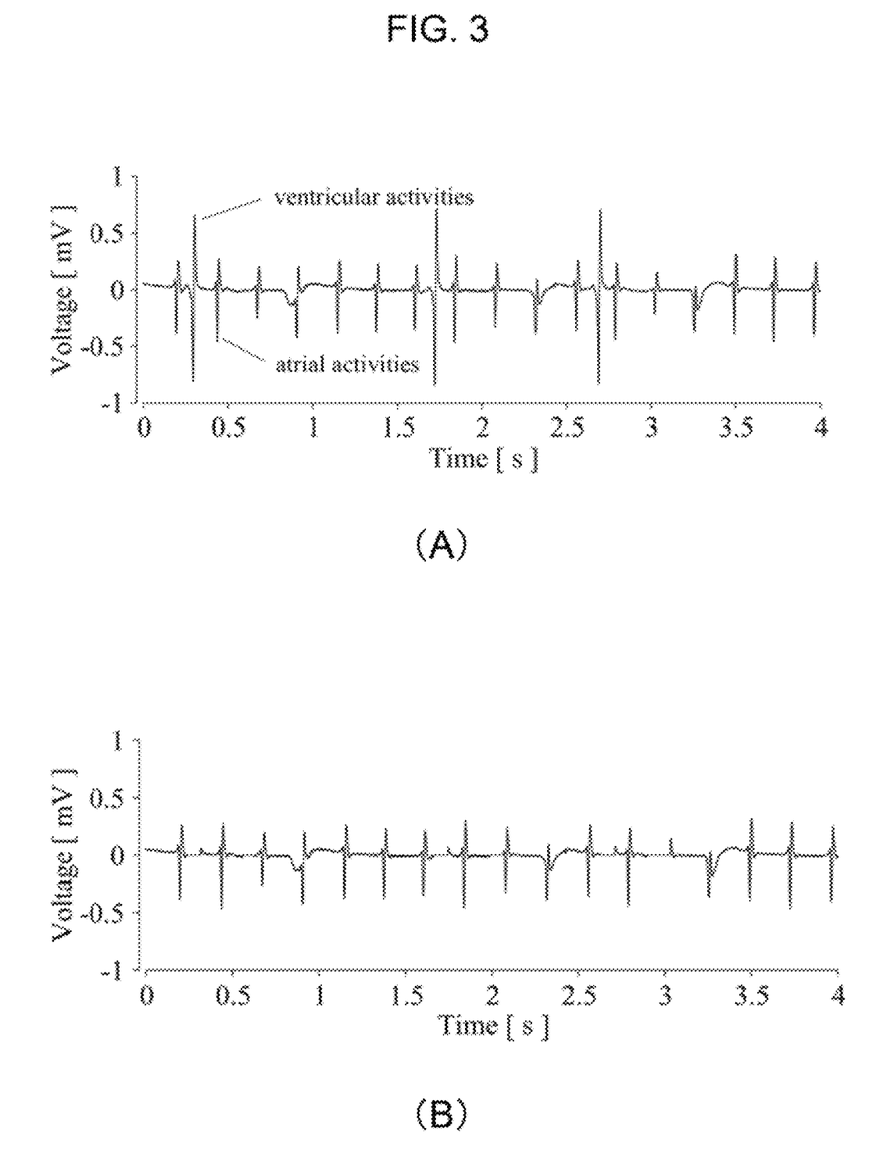
FIG. 3 is graphs illustrating electrocardiograms of a subject who suffers from the continuous atrial fibrillation.

The electrocardiogram measured at the atrium and the electrocardiogram after the removal of the ventricle waves are indicated respectively in FIG. 3(A) and FIG. 3(B). FIG. 3(B) is the atrial electric potential from which the ventricle waves in FIG. 3(A) are removed.

The complex fractionated atrial electrogram judgment unit 20 judges, as illustrated in FIG. 3(B), the atrial waves with short intervals and the continuous electric potential, which are the characteristics of the complex fractionated atrial electrogram, by using the electrocardiogram data obtained by executing ventricle wave removal processing on the measured electrocardiogram data.

The complex fractionated atrial electrogram judgment unit 20 judges the atrial waves with short intervals, that is, one of the characteristics of the complex fractionated atrial electrogram by using the atrial wave interval judgment algorithm. Specifically speaking, the part(s) where the interval of the atrial waves is less than 120 [ms] as illustrated in FIG. 2(B) is judged.

Firstly, the complex fractionated atrial electrogram judgment unit 20 squares the electric potential $e_1(t)$ in order to emphasize the difference between the atrial waves and the continuous electric potential in the electrocardiogram data and make the electric potential a positive value. The complex fractionated atrial electrogram judgment unit 20 judges the interval between the atrial waves with respect to $e_1(t)^2$. Since a voltage value of the atrial waves fluctuates significantly depending on a measurement site, a muscle mass of the heart, and so on, it is necessary to generate a threshold value for each waveform. So, a threshold value $e_{th1}$ is generated for each squared electric potential $e_1(t)^2$ by using distribution of the electric potential $e_1(t)$ and the threshold value $e_{th1}$ is defined by the following expression (1).

[Math. 1]

$$e_{th1} = V(e_1(t) \times K_1 \qquad (1)$$

Figure 4:
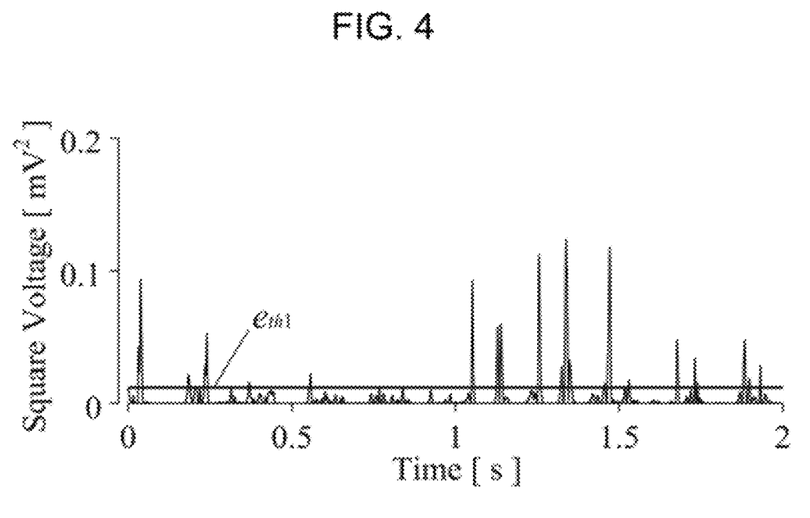
FIG. 4 is a graph illustrating an electrocardiogram of the subject before and after removal of atrial waves.
Figure 5:
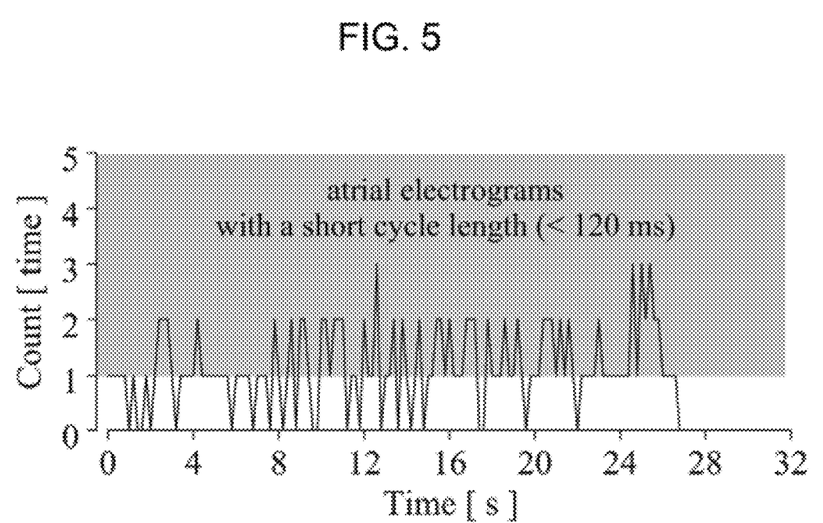
FIG. 5 is a graph for explaining a judgment result of the atrial waves in excess of a threshold value.

FIG. 4 illustrates the squared electric potential $e_1(t)^2$ and the threshold value $e_{th1}$ with respect to FIG. 2(B). The number of times when the squared electric potential $e_1(t)^2$ exceeds the threshold value $e_{th1}$ with an interval of 200 [ms] is found by using this atrial wave interval judgment algorithm. FIG. 5 illustrates the result of finding the number of times when the squared electric potential $e_1(t)^2$ exceeds the threshold value $e_{th1}$ with respect to FIG. 2(B).

If the number of times in excess of the threshold value is twice or more here, the interval of the atrial waves becomes less than 120 [ms] and it is judged as the atrial waves with short intervals. A value $I_1$ is calculated by integrating the number of times in excess of the threshold value with regard to, for example, the part hatched in FIG. 5 regarding which the number of times in excess of the threshold value is twice or more. As the value $I_1$ becomes larger, it indicates that the atrial waves with short intervals, that is, the characteristic of the complex fractionated atrial electrogram exists.

A parameter $K_1$ for deciding a minimum value of the atrial waves is set from the judgment results using a total of 30 electrocardiograms obtained by measuring three continuous atrial fibrillation patients (two males and a one female with an average age of 59±6.4). The parameter $K_1$ is set as $K_1=3$ where a proper diagnosis rate of the atrial waves detected by this atrial wave interval judgment algorithm relative to the atrial waves judged by the doctor becomes 100[%].

Figure 6:
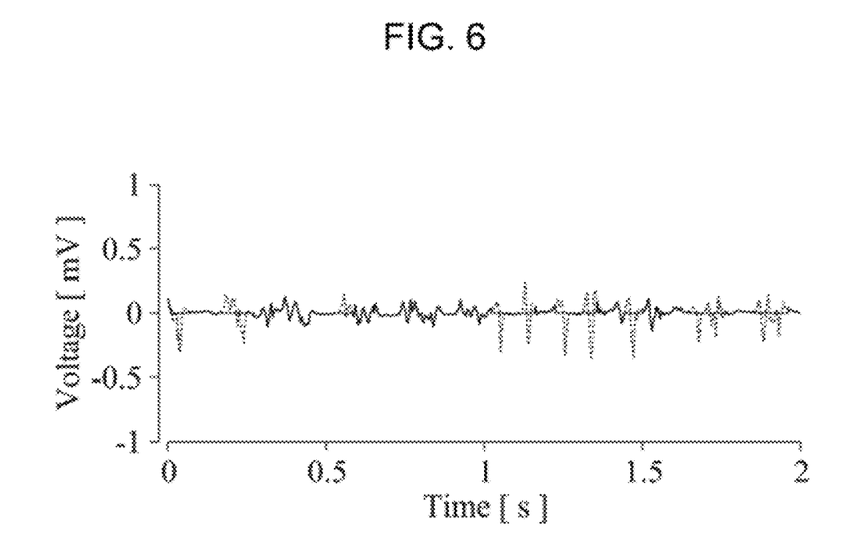
FIG. 6 is a graph illustrating a complex fractionated atrial electrogram after removing the atrial waves.

Subsequently, the complex fractionated atrial electrogram judgment unit 20 judges the continuous electric potential indicated in FIG. 2(B) and FIG. 2(C) by using a continuous electric potential judgment algorithm. The continuous electric potential is the atrial electric potential which is continuously measured; however, it is necessary here to distinguish the continuous electric potential from the atrial electric potential (atrial waves) with a large amplitude. Therefore, the atrial waves judged by the continuous electric potential judgment algorithm are removed from the electric potential, thereby avoiding the judgment of the atrial waves by the algorithm. FIG. 6 indicates the electric potential $e_2(t)$, from which the atrial waves judged by the continuous electric potential judgment algorithm are removed, with a solid line and the removed atrial waves with a dashed line, respectively.

The continuous electric potential is a continuously fluctuating atrial electric potential and its voltage value fluctuates depending on the measurement site, the muscle mass of the heart, and so on. So, a threshold value is generated from the maximum value of the atrial waves and the part(s) in excess of the threshold value is judged as the continuous electric potential. A threshold value $e_{th2}$ for judging the continuous electric potential from the maximum value $e_{maximum}$ of the atrial waves is defined according to the following expression (2).

[Math. 2]

$$e_{th2} = e_{maximum} \times K_2 \qquad (2)$$

An integrated value of the number of times in excess of the threshold value is calculated as a value $I_2$ with respect to the set threshold value. The value $I_2$ represents the duration of the continuous electric potential; and as the value $I_2$ becomes larger, it indicates that the electric potential is a continuous and stable complex fractionated atrial electrogram.

Figure 7:
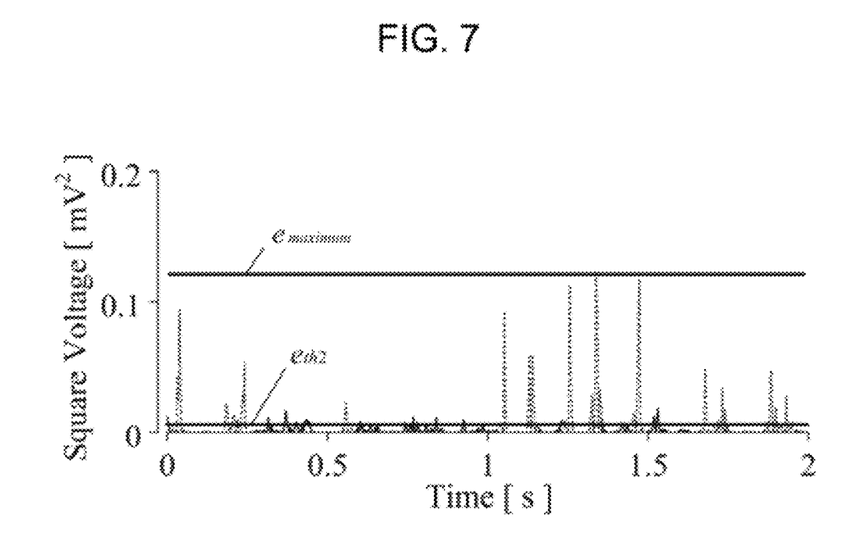
FIG. 7 is a graph illustrating calculation results of the second power of an electric potential and a threshold value after removing the atrial waves.

A parameter $K_2$ for deciding a maximum value of the continuous electric potential is set from the judgment using a total of 30 electrocardiograms similar to those of the parameter $K_1$. The parameter $K_2$ is set as $K_2=1/40$ where a proper diagnosis rate of the continuous electric potential judged according to the results of the judgment by the doctor as the electric potential in which no continuous electric potential is seen, and the electric potential in which the continuous electric potential is seen, and the continuous electric potential judged according to the continuous electric potential judgment algorithm becomes the highest, that is, 93[%]. FIG. 7 illustrates the result of calculating the second power of an electric potential $e_2(t)_2$ and a threshold value $e_{th2}$ with respect to the electric potential $e_2(t)$ from which the atrial waves in FIG. 6 have been removed.

The complex fractionated atrial electrogram judgment unit 20 judges the complex fractionated atrial electrogram from the two items, that is, the atrial waves with short intervals and the continuous electric potential which are the characteristics of the complex fractionated atrial electrogram by using the value $I_1$ calculated according to the atrial wave interval judgment algorithm and the value $I_2$ calculated according to the continuous electric potential judgment algorithm. The value $I_1$ reflects the occurrence frequency of the atrial waves with short intervals and the value $I_2$ reflects the duration of the continuous electric potential.

Subsequently, the complex fractionated atrial electrogram judgment unit 20 calculates a value (occurrence frequency value) Q which indicates the occurrence frequency of the two characteristics of the complex fractionated atrial electrogram according to Expression (3) below, from the value $I_1$ and the value $I_2$, in which the two items, that is, the atrial waves with short intervals and the continuous electric potential which are the characteristics of the complex fractionated atrial electrogram are reflected, and measurement time $t_m$.

[Math. 3]

$$Q = \frac{I_1}{t_m} \times \frac{I_2}{t_m} \qquad (3)$$

This method is to set a threshold value $Q_{Threshold}$ to the value Q in which the atrial waves with short intervals and the continuous electric potential are reflected, and perform an automatic judgment of whether it is the complex fractionated atrial electrogram or is not the complex fractionated atrial electrogram. In a case of $Q \leq Q_{Threshold}$, that electric potential is judged as being not the complex fractionated atrial electrogram; and in a case of $Q > Q_{Threshold}$, it is judged as being the complex fractionated atrial electrogram.

Figure 9:
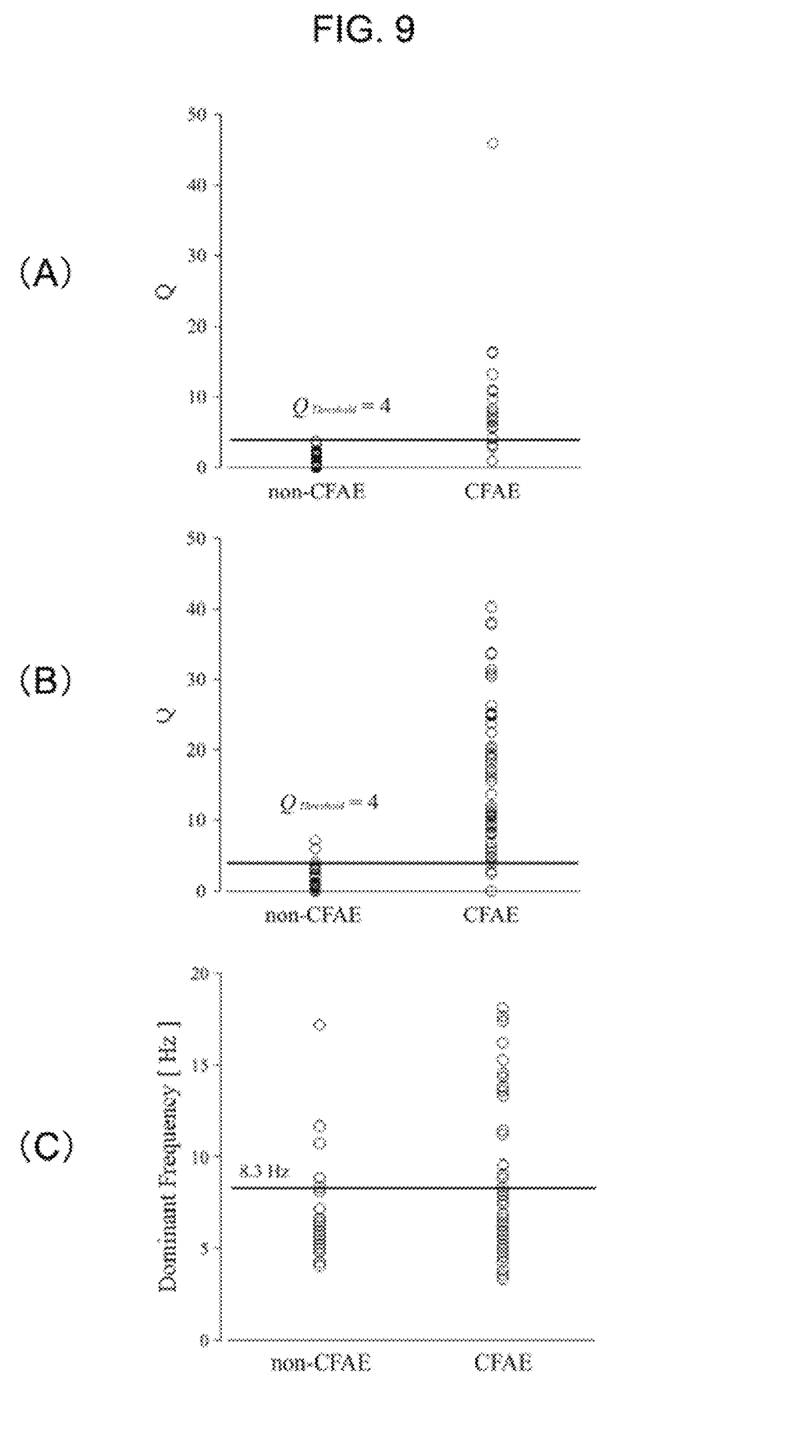
FIG. 9 is graphs for explaining an occurrence frequency value.

Regarding the threshold value $Q_{Threshold}$ for judging whether the relevant electric potential is not the complex fractionated atrial electrogram or is the complex fractionated atrial electrogram, the value Q was calculated regarding 53 electric potentials (the complex fractionated atrial electrograms: 20; and not the complex fractionated atrial electrograms: 33) measured from seven continuous atrial fibrillation patients (6 males and one female with an average age of 56±7.8) who are not the three target patients for setting the parameters $K_1$, $K_2$ and the threshold value $Q_{Threshold}$ was set as $Q_{Threshold}$=4 where the proper diagnosis rate for judging whether the relevant electric potential is the complex fractionated atrial electrogram or is not the complex fractionated atrial electrogram becomes the highest, that is, 94[%]. FIG. 9(A) illustrates the results of the value Q calculated by this method with respect to the 53 electric potentials (the complex fractionated atrial electrograms: 20; and not the complex fractionated atrial electrograms: 33).

Figure 8:
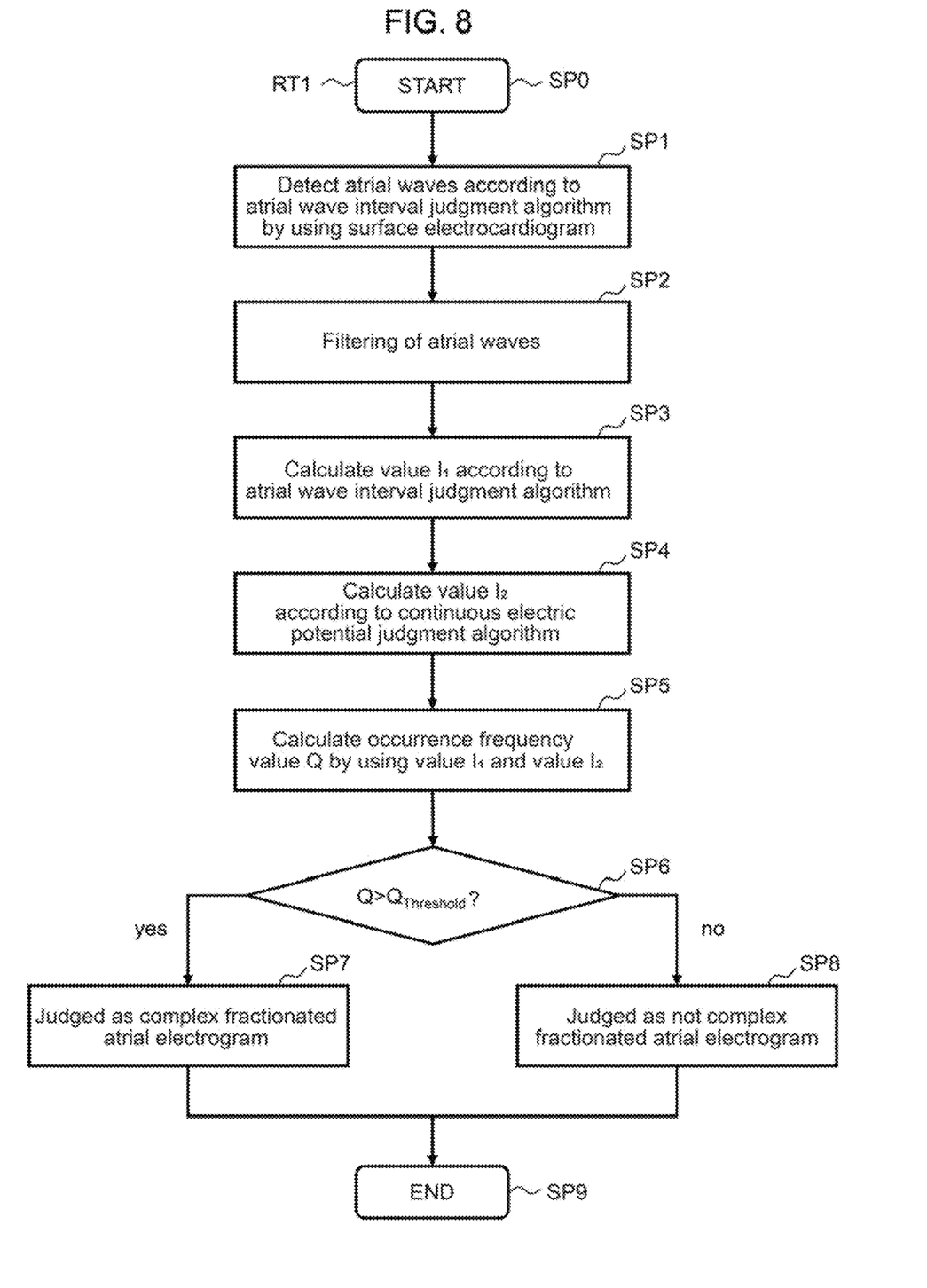
FIG. 8 is a flowchart for explaining complex fractionated atrial electrogram judgment processing.

FIG. 8 illustrates a flowchart of the judgment of whether the relevant electric potential is the complex fractionated atrial electrogram or it is not the complex fractionated atrial electrogram by the complex fractionated atrial electrogram judgment unit 20. After receiving the electrocardiogram data from the communication terminal unit 3 which the subject wears, the complex fractionated atrial electrogram judgment unit 20 in the control apparatus 11 for the information management apparatus 10 starts a complex fractionated atrial electrogram judgment processing procedure RT1 illustrated in FIG. 8 from step SP0.

The complex fractionated atrial electrogram judgment unit 20 detects the atrial waves according to the atrial wave interval judgment algorithm using the subject's surface electrocardiogram (the electrocardiogram measured at the body surface) (step SP1) and then removes the atrial waves by filtering (step SP2).

Subsequently, the complex fractionated atrial electrogram judgment unit 20 calculates the value $I_1$, in which the occurrence frequency of the atrial waves is reflected, according to the atrial wave interval judgment algorithm (step SP3) and then calculates the value $I_2$, in which the duration of the continuous electric potential is reflected, according to the continuous electric potential judgment algorithm (step SP4).

Then, the complex fractionated atrial electrogram judgment unit 20 calculates the occurrence frequency value Q by using the value $I_1$ and the value $I_2$ (step SP5) and then compares the occurrence frequency value Q with the predetermined threshold value $Q_{Threshold}$ which is an automatic judgment criterion (step SP6).

If the occurrence frequency value Q is larger than the threshold value in this step SP6, the complex fractionated atrial electrogram judgment unit 20 judges it as the complex fractionated atrial electrogram (step SP7); and on the other hand, if the occurrence frequency value Q is equal to or smaller than the threshold value, the complex fractionated atrial electrogram judgment unit 20 judges it as being not the complex fractionated atrial electrogram (step SP8) and terminates this processing procedure RT1 (step SP9).

The effectiveness of the method according to the present invention is verified by actually performing an experiment described below. Specifically, the effectiveness of the present invention was verified through the experiment of performing the automatic judgment with respect to the electrocardiograms measured from inside hearts of eight continuous atrial fibrillation patients (6 males and 2 females with an average age of 60±10) who are not the target patients for setting the parameters $K_1$, $K_2$ and the threshold value $Q_{Threshold}$.

A total of 100 electrocardiograms which were measured for 4 seconds to 32 seconds were used as the electrocardiograms. A doctor(s) judged whether the relevant electric potential is the complex fractionated atrial electrogram or is not the complex fractionated atrial electrogram, with respect to each electric potential in accordance with the definition of the complex fractionated atrial electrogram, that is, the continuous electric potential regarding which the interval of the atrial waves is less than 120 [ms] exists. As a result, regarding the total of 100 electric potentials, 62 electric potentials were the complex fractionated atrial electrograms and 38 electric potentials were not the complex fractionated atrial electrograms. The automatic judgment of whether the relevant electric potential is the complex fractionated atrial electrogram or is not the complex fractionated atrial electrogram was conducted by using these 100 electric potentials.

The automatic judgment of whether the relevant electric potential is the complex fractionated atrial electrogram or is not the complex fractionated atrial electrogram was conducted by using this method of judging the complex fractionated atrial electrogram from the two items, that is, the atrial waves with short intervals and the continuous electric potential which are the characteristics of the complex fractionated atrial electrogram and the effectiveness of the method according to the present invention was verified with respect to the automatic judgment of the complex fractionated atrial electrogram of the atrial fibrillation from the proper diagnosis rate which is the result of the automatic judgment.

An analysis was performed by a judgment method by means of Fast Fourier Transform (FFT) which is a conventional technology. Regarding a DF (Dominant Frequency) regarding which a power spectrum becomes maximum at the frequency of 20 [Hz] or less, 8.3 [Hz] was decided as a threshold value of DF because the interval of the atrial waves which is the characteristic of the complex fractionated atrial electrogram is less than 120 [ms]. The electric potential whose DF was less than 8.3 [Hz] was judged as being not the complex fractionated atrial electrogram, and the electric potential whose DF was equal to or more than 8.3 [Hz] was judged as being the complex fractionated atrial electrogram. The effectiveness is verified according to the proper diagnosis rate of this proposed method and that of the conventional method.

The result of the automatic judgment of whether the relevant electric potential is the complex fractionated atrial electrogram or is not the complex fractionated atrial electrogram by using the method according to the present invention will be indicated below. FIG. 9(B) shows values of Q calculated by this method with respect to a total of 100 electrocardiogram signals (the complex fractionated atrial electrograms: 62; and not the complex fractionated atrial electrograms: 38) measured from atriums of eight continuous atrial fibrillation patients. Consequently, it was judged that a positive predictive value was 97[%], a negative predictive value was 88[%], and the proper diagnosis rate (accuracy) was 93[%] with respect to the total of the 100 electric potentials (the complex fractionated atrial electrograms: 62; and not the complex fractionated atrial electrograms: 38).

FIG. 9(C) shows the results of calculating DF by an analysis method using FFT with respect to the total of 100 electric potentials (the complex fractionated atrial electrograms: 62; and not the complex fractionated atrial electrograms: 38) similarly measured from the atriums of the eight continuous atrial fibrillation patients. As a result of the automatic judgment from DF calculated by the analysis method using FFT, it was successively judged that the positive predictive value was 71[%], the negative predictive value was 42[%], and the proper diagnosis rate was 50[%] with respect to the total of the 100 electric potentials (the complex fractionated atrial electrograms: 62; and not the complex fractionated atrial electrograms: 38).

By comparing the method according to the present invention with the conventional method, the automatic judgment of whether the relevant electric potential is the complex fractionated atrial electrogram or is not the complex fractionated atrial electrogram was successfully performed with higher accuracy by the method according to the present invention with respect to all the positive predictive value, the negative predictive value, and the proper diagnosis rate.

Furthermore, sensitivity of the conventional method indicating the predictive value of the automatic judgment with respect to the complex fractionated atrial electrogram was 32[%] as illustrated in FIG. 9(C), while the sensitivity of the proposed method of the result of the automatic judgment with respect to the complex fractionated atrial electrogram was 922[%] as illustrated in FIG. 9(B). This result shows that as compared to the conventional method of judging the intervals of the atrial waves, the method according to the present invention for judging the complex fractionated atrial electrogram from the two items, that is, the atrial waves with short intervals and the continuous electric potential can judge the complex fractionated atrial electrogram with much higher accuracy than the complex fractionated atrial electrogram defined by the conventional method.

(3) Assessment Learning of the Degree of Progress of Atrial Fibrillation According to this Embodiment The complex fractionated atrial electrogram judgment unit 20 judges whether the relevant electric potential is the complex fractionated atrial electrogram or is not the complex fractionated atrial electrogram as described above, and stores the judgment data indicating the result of the above-mentioned judgment in the data storage unit 13. Then, the frequency histogram generation unit 21 generates the frequency histogram according to the occurrence frequency within a specified period of time on the basis of the judgment data collected over the specified period of time with respect to the subject and read from the data storage unit 13.

The assessment learning unit 22 performs the assessment learning for assessing the degree of progress of the atrial fibrillation, which the subject suffers from, on the basis of the frequency histogram with respect to the subject by the frequency histogram generation unit 21. Specifically, the assessment learning unit 22 assesses and learns the degree of progress of the atrial fibrillation of the subject on the basis of the frequency histogram obtained by collecting the judgment results of the complex fractionated atrial electrogram, which serves as a measurement index for finding the ablation site of the percutaneous catheter myocardial ablation, over a specified period of time.

As a result, it becomes possible to support the doctor(s) so that they can accurately diagnose the continuous atrial fibrillation even under the condition where the subject themselves cannot recognize it.

(4) Diagnosis Method by Doctor(s)

With the diagnosis support system 1, the doctor(s) diagnoses the degree of progress of the atrial fibrillation of the subject by using the doctor's-side terminal unit 30. With the doctor's-side terminal unit 30, the doctor inputs the degree of progress of the atrial fibrillation, which the subject suffers from, as the diagnosis result by using the input unit 33 while visually checking the frequency histogram in the state where the frequency histogram concerning the subject by the frequency histogram generation unit 21 is displayed on the display unit 32.

The terminal control unit (criterion function generation unit) 34 generates a criterion function indicating a criterion for assessing the degree of the atrial fibrillation by referring to the result of the assessment learning by the assessment learning unit 22 and the diagnosis result of the doctor by the input unit 33 with respect to the subject.

As a result, with the diagnosis support system 1, as the doctor inputs, via the input unit 33, the degree of progress of the atrial fibrillation of the subject over the specified period of time while visually checking the frequency histogram of the subject which is displayed on the display unit 32, it is possible to significantly enhance the accuracy of the assessment learning for assessing the degree of progress of the atrial fibrillation which the subject suffers from.

(5) Other Embodiments

Incidentally, this embodiment has described the aforementioned case where the diagnosis support system 1 is mounted on the subject by attaching the electrocardiogram sensor 2 to the subject's chest contactlessly and attaching the communication terminal unit 3 to the subject's wrist; however, the present invention is not limited to this example and may be applied to a wide variety of other configurations as long as it can measure the electrocardiogram noninvasively from the subject's body surface. However, it is desirable that a configuration which would cause less physical load as possible to the subject be employed in order to enable continuous measurement for a specified period of time (four weeks).

Furthermore, this embodiment has described the case where the frequency histogram generation unit 21 sets four weeks as the specified period of time to collect the judgment data concerning the subject in order to generate the frequency histogram; however, the present invention is not limited to this example and an optimum data collection period may be set as the specified period of time upon consultation with the doctor as long as the specified period of time is one week or longer.

REFERENCE SIGNS LIST

1: diagnosis support system
2: electrocardiogram sensor (electrocardiogram measurement unit)
3: communication terminal unit
4: communication network
10: information management apparatus
11: control apparatus
12, 31: communication interface
13: data storage unit
20: complex fractionated atrial electrogram judgment unit
21: frequency histogram generation unit
22: assessment learning unit
30: doctor's-side terminal unit
32: display unit
33: input unit
34: terminal control unit
RT1: complex fractionated atrial electrogram judgment processing procedure

The invention claimed is:

1. A diagnosis support system comprising:
   an electrocardiogram measurement unit that measures an electrocardiogram of a subject;
   a complex fractionated atrial electrogram judgment unit that judges a complex fractionated atrial electrogram indicating characteristics of an atrial fibrillation at a heartbeat interval that is a peak interval of R waves which are chronologically adjacent to each other, on a basis of electrocardiogram data measured by the electrocardiogram measurement unit, the complex fractionated atrial electrogram having an atrial electric potential more than a threshold value that is generated from a maximum value of atrial waves;
   a data storage unit that stores judgment results by the complex fractionated atrial electrogram judgment unit in chronological order as judgment data which is specific to the subject;
   a frequency histogram generation unit that generates a frequency histogram according to an occurrence frequency within a specified period of time on a basis of the judgment data which is collected over the specific period of time with respect to the subject and read from the data storage unit; and
   an assessment learning unit that performs assessment learning to assess a degree of progress of an atrial fibrillation on a basis of the frequency histogram with respect to the subject by the frequency histogram generation unit,
   wherein the complex fractionated atrial electrogram judged by the complex fractionated atrial electrogram judgment unit comprises a measurement for finding an ablation site of the percutaneous catheter myocardial ablation;
   wherein atrial fibrillation is ablated according to the found ablation site.

2. The diagnosis support system according to claim 1, wherein the complex fractionated atrial electrogram judged by the complex fractionated atrial electrogram judgment unit is a combination of an occurrence frequency of the atrial waves and the atrial electric potential which occurs continuously.

3. The diagnosis support system according to claim 1, comprising:
   a display unit that displays the frequency histogram with respect to the subject by the frequency histogram generation unit;
   an input unit to input the degree of progress of the atrial fibrillation as a diagnosis result with respect to the frequency histogram displayed on the display unit; and
   a criterion function generation unit that generates a criterion function indicating a criterion for assessing the degree of progress of the atrial fibrillation by referring to a result of the assessment learning by the assessment learning unit and the diagnosis result of the input by the input unit with respect to the subject.

4. The diagnosis support system according to claim 3, comprising a progress degree assessment unit that assesses the degree of progress of the atrial fibrillation from the frequency histogram with respect to the subject by the frequency histogram generation unit by means of the criterion function generated by the criterion function generation unit.

5. The diagnosis support system according to claim 3, wherein the degree of progress of the atrial fibrillation is a degree of progress of a state where a baseline for an electrocardiogram waveform based on the electrocardiogram data fluctuates finely and no P wave exists and the heartbeat interval is irregular.

6. A diagnosis support method comprising:
   a first step of judging a complex fractionated atrial electrogram indicating characteristics of an atrial fibrillation at a heartbeat interval that is a peak interval of R waves which are chronologically adjacent to each other, on a basis of electrocardiogram data obtained by measuring an electrocardiogram of a subject, the complex fractionated atrial electrogram having an atrial electric potential more than a threshold value that is generated from a maximum value of atrial waves;
   a second step of storing judgment results by the first step as judgment data, which is specific to the subject, in chronological order in a data storage unit;
   a third step of generating a frequency histogram according to an occurrence frequency within a specified period of time on a basis of the judgment data which is collected over the specific period of time with respect to the subject and read from the data storage unit;
   a fourth step of performing assessment learning to assess a degree of progress of an atrial fibrillation on a basis of the frequency histogram with respect to the subject by the third step,
      wherein the complex fractionated atrial electrogram judged by the complex fractionated atrial electrogram judgment unit comprises a measurement for finding an ablation site of the percutaneous catheter myocardial ablation over time;
      wherein atrial fibrillation is ablated according to the found ablation site.

7. The diagnosis support method according to claim 6, wherein the complex fractionated atrial electrogram judged by the first step is a combination of an occurrence frequency of the atrial waves and the atrial electric potential which occurs continuously.

8. The diagnosis support method according to claim 6, comprising:
   a fifth step of displaying the frequency histogram with respect to the subject by the third step on a display unit and letting input the degree of progress of the atrial fibrillation as a diagnosis result with respect to the frequency histogram displayed on the display unit; and
   a sixth step of generating a criterion function indicating a criterion for assessing the degree of progress of the atrial fibrillation by referring to a result of the assessment learning by the fourth step and a diagnosis result of the input by the fifth step with respect to the subject.

9. The diagnosis support method according to claim 8, comprising a seventh step of assessing the degree of progress of the atrial fibrillation from the frequency histogram with respect to the subject by the third step by means of the criterion function generated by the sixth step.

10. The diagnosis support method according to claim 6, wherein the degree of progress of the atrial fibrillation is a degree of progress of a state where a baseline for an electrocardiogram waveform based on the electrocardiogram data fluctuates finely and no P wave exists and the heartbeat interval is irregular.

* * * * *